US012576027B2

(12) United States Patent
Puppini et al.

(10) Patent No.: US 12,576,027 B2
(45) Date of Patent: Mar. 17, 2026

(54) DICLOFENAC TOPICAL FORMULATION WITH A HIGH ABSORPTION RATE

(71) Applicant: IBSA INSTITUT BIOCHIMIQUE SA, Lugano (CH)

(72) Inventors: Nadia Puppini, Lugano (CH); Valentina Nicolini, Lugano (CH); Tiziano Fossati, Lugano (CH)

(73) Assignee: IBSA INSTITUT BIOCHIMIQUE SA, Lugano (CH)

( * ) Notice: Subject to any disclaimer, the term of this patent is extended or adjusted under 35 U.S.C. 154(b) by 236 days.

(21) Appl. No.: 18/567,421

(22) PCT Filed: Jun. 22, 2022

(86) PCT No.: PCT/EP2022/067018
§ 371 (c)(1),
(2) Date: Dec. 6, 2023

(87) PCT Pub. No.: WO2022/268882
PCT Pub. Date: Dec. 29, 2022

(65) Prior Publication Data
US 2024/0269068 A1      Aug. 15, 2024

(30) Foreign Application Priority Data

Jun. 25, 2021    (IT) ........................ 102021000016751

(51) Int. Cl.
*A61K 9/06*            (2006.01)
*A61K 9/00*            (2006.01)
*A61K 31/196*        (2006.01)
*A61K 47/24*          (2006.01)

(52) U.S. Cl.
CPC .............. *A61K 9/06* (2013.01); *A61K 9/0014* (2013.01); *A61K 31/196* (2013.01); *A61K 47/24* (2013.01)

(58) Field of Classification Search
None
See application file for complete search history.

(56) References Cited

U.S. PATENT DOCUMENTS

2015/0297507 A1    10/2015    Grenier et al.

FOREIGN PATENT DOCUMENTS

| CN | 105395544 | * | 3/2016 |
| CN | 105395544 | A | 3/2016 |
| EP | 0372527 | A1 | 6/1990 |
| EP | 0271709 | B1 | 5/1991 |

OTHER PUBLICATIONS

A. Fini, et al., "Diclofenac/N-(2-Hydroxyethyl)Pyrrolidine: A New Salt for an Old Drug", Drugs Exptl Cun Res, vol. 19, No. 3, pp. 81-88, 1993.
International Search Report and Written Opinion for Corresponding International Application No. PCT/EP2022/067018, 9 pages, Sep. 6, 2022.
International Preliminary Report on Patentability for Corresponding International Application No. PCT/EP2022/067018, 16 Pages, Sep. 28, 2023.

* cited by examiner

*Primary Examiner* — Nannette Holloman
(74) *Attorney, Agent, or Firm* — LUCAS & MERCANTI, LLP

(57) ABSTRACT

Pharmaceutical compositions for topical use containing diclofenac in the form of salt with epolamine, present at concentrations higher than 2.0% by weight are described. Such compositions provide, with respect to those currently available, a more complete absorption of the administered dose, reducing the dispersion of active ingredient and allowing treatments requiring the administration of high and accurate dosages to be carried out.

6 Claims, No Drawings

DICLOFENAC TOPICAL FORMULATION WITH A HIGH ABSORPTION RATE

CROSS-REFERENCE TO RELATED APPLICATIONS

This application is a 371 of PCT/EP2022/067018, filed Jun. 22, 2022, which claims the benefit of Italian Patent Application No. 102021000016751, filed Jun. 25, 2021.

FIELD OF THE INVENTION

The present invention relates to the field of anti-inflammatory active ingredients for topical use and formulations containing them.

BACKGROUND OF THE INVENTION

Diclofenac, i.e. 2-[(2,6-dichlorophenyl)-amino]benzeneacetic acid, is an active ingredient widely used in anti-inflammatory, antirheumatic, antipyretic and analgesic treatment. The most common indications are acute pain and inflammation in rheumatoid arthritis, ankylosing spondylitis, arthrosis, non-joint rheumatism, and other musculoskeletal diseases, such as lumbosciatalgia; it is also used in acute gout, post-operative pain, actinic keratosis, allergic conjunctivitis, dysmenorrhea, and inflammation secondary to trauma, etc.

When orally administered, diclofenac is absorbed in an almost complete way, due to the presence of optimal conditions of pH and enzymes favoring its assimilation; high hematic peaks within about 2 hours from administration are reached.

The topical administration shows high absorption difficulties due to the poor capacity of diclofenac to solubilize at neutral or close to neutrality pH (characteristic condition of carriers for topical use) and to permeate the stratum corneum of the skin. It is known from EP 271 709 B11, on behalf of the Applicant, to improve diclofenac solubility by forming its salts with an organic base, in particular hydroxyethyl pyrrolidine (epolamine). Based on this principle, topical formulations of diclofenac were realized which, also due to the co-presence of emollients with a surfactant function as lecithin, provide an appropriate penetration capacity; in fact, it is known that diclofenac-epolamine forms micellar structures with lecithin able to intercalate in the structure of cellular membranes of the stratum corneum, thus favoring the absorption process of this drug; at the same time, lecithin exerts a hydrating action on skin, further favoring penetration of diclofenac-epolamine (*Drugs Exptl.Clin.Res.*, 1993, XIX(3), pp. 81-88). Topical formulation containing an average of 1-1.5% diclofenac-epolamine and lecithin are commercially available. However, such formulations are not entirely satisfactory from the point of view of the absorption of the active ingredient. Carrying out a possible second topical administration is not a valid solution since it stratifies on a surface which is already saturated with diclofenac and therefore not suitable to absorb more, resulting in an even greater dispersion of the active ingredient, with corresponding waste of product and uncertainty of the actually administered dosage. The present invention answers the need of new topical formulations of diclofenac-epolamine having optimal characteristics of absorption of the active ingredient.

SUMMARY OF THE INVENTION

In the context of research conducted by the Applicant, it has now been surprisingly found, and it is an object of the present invention, that in formulations for topical use wherein diclofenac-epolamine is present at concentrations equal to at least 2% by weight, the entity (rate) of diclofenac absorption by the skin is unexpectedly high: in particular, it increases in a super-proportional way with respect to the increase of the diclofenac concentration in the carrier: a topical absorption significantly higher than that calculable for proportionality based on the greater amount of diclofenac is thus obtained. The found effect is even more surprising considering that, in the tested formulations of the invention, the amount of lecithin was not increased with respect to that of the reference formulation containing 1.3% diclofenac-epolamine: in the present compositions the incidence of the micellar component favoring the absorption was therefore reduced, operating in potentially more disadvantageous conditions for absorption. Nonetheless, due to the higher absorption rate herein provided it is possible to optimally carry out treatments requiring the administrations of high and accurate diclofenac dosages.

DETAILED DESCRIPTION OF THE INVENTION

In this text, all the percentages referring to the concentrations of substances are understood to be calculated as weight/weight on the total weight of the composition, unless otherwise indicated.

Unless differently indicated, all percentage values herein indicated are not strictly intended, but are intended to be approximate variables within a range of ±0.2%, for example a value of 5% comprises all values from 4.8% to 5.2%. For all the given ranges, the upper and lower limits of the range are meant to be included in the range; in a more limited sub-embodiment, the upper and lower limits are excluded.

All the concentrations herein reported for diclofenac-epolamine are intended to be calculated on the product itself as a salt (and not as diclofenac per se).

In the pharmaceutical compositions according to the present invention, diclofenac was used in the form of salt with epolamine (hydroxyethyl pyrrolidine); in such salt, herein briefly indicated with "diclofenac-epolamine" or "DHEP", diclofenac and epolamine are typically combined in a 1:1 molar ratio; however, such ratio is not limitative and can be varied according to needs, for example in the range between 0.5:1 and 1:0.5. Salts of diclofenac-epolamine are commercially available; the preparation of such salts is described, for example, in the patent EP 271 709 B1, herein incorporated by reference.

The term diclofenac "absorption" means the ability of diclofenac to permeate the stratum corneum of the skin, measurable as amount of diclofenac permeated in a standard IVPT test, as shown in Experimental; the percentage of absorption is herein always formally calculated as diclofenac in the form of salt with epolamine.

In the present compositions, the concentration by weight of diclofenac-epolamine, has to be at least 2.0% by weight, and preferably higher than 2.0%; in fact, at lower concentrations, the increase of the degree of diclofenac absorption as a function of its concentration is not fulfilled or is not significantly observable. The upper limit of concentration of diclofenac is not strictly fixed and can be varied; from a practical point of view, however, in topical compositions of sodium diclofenac only occasionally 5% is exceeded (corresponding to 6.5% diclofenac-epolamine); therefore, an upper limit of concentration of diclofenac-epolamine according to the invention could be, for example, 7.0%.

Optimal operating ranges for the concentration of diclofenac-epolamine can generally range between 2.0 and 5.5%, preferably between 2.0 and 3.0%.

Particularly effective concentration values are between 2.3 and 2.9%, in particular between 2.5 and 2.7%, optimally equal to 2.6%; these concentration values and ranges of diclofenac-epolamine are best used in compositions of the invention further including lecithin, particularly those where the lecithin is in a weight ratio lower than 1:1 (e.g. 0.5:1 to 0.9:1) with respect to diclofenac-epolamine. These compositions have been found particularly effective to obtain skin permeation of diclofenac-epolamine, despite the lowered emulsifying contribute contribution of the lecithin, which is usually co-formulated with diclofenac in 1:1 or much higher weight ratios.

The present compositions of diclofenac-epolamine can be realized in any pharmaceutical form suitable for topical administration: examples of such forms are creams, ointments, pastes and gels, in particular hydrogels i.e. water-based gels. The pharmaceutical form can be also a solution (for example, a tincture or a spray solution), or even a sprinkling powder; it can be also a plaster, a bandage or a film for transdermal applications, each containing diclofenac-epolamine. In the case in which the pharmaceutical form includes a physical support impregnated with diclofenac-epolamine, (for example a plaster, bandage, etc.) the aforesaid concentrations of diclofenac-epolamine are meant to be referred to the impregnating solution.

The compositions in object also include the following conventional ingredients: a suitable carrier for transdermal applications and, optionally, further excipients as a function of the pharmaceutical form type and the properties desired for it. The pharmaceutical carrier can be water or, more preferably, an aqueous system as a hydrogel, or any other base for topical formulation, for example a base for creams, ointments, etc.

Emollients with also a surfactant function (emulsifier) in particular lecithin, can be present: however, it was noted that the aforementioned effects of high permeation occur with emulsifier concentrations even lower than those required for a complete emulsion of the present diclofenac-epolamine, such as observed using a lecithin/diclofenac-epolamine weight ratio lower than 1:1, which is the value normally used in the commercial reference gel. This aspect was found particularly surprising since from literature lecithin is normally known to enhance the permeation of diclofenac-epolamine through the stratum corneum, while in the present compositions an increase of permeation was found as reducing the lecithin/diclofenac-epolamine ratio with respect to the commercial reference.

The further excipients present in the composition can be suitably selected based on standard criteria according to the chosen pharmaceutical form and the particular additional properties desired for it. Examples of such excipients can be, for example, co-emulsifiers, thickeners, gelling agents, humectants, tonicity regulating agents, pH adjusting agents, stabilizers, antioxidants, chelators, film-forming polymers, (further) permeation agents, dyes, perfumes, etc.

In some embodiments, the compositions containing at least 2% by weight of diclofenac-epolamine according to the invention comprise a hydrogel as a carrier and lecithin as an emollient/surfactant.

In some embodiments, the compositions containing at least 2% by weight of diclofenac-epolamine according to the invention comprise, besides a hydrogel as a carrier and lecithin as an emollient/surfactant, one or more among emulsifiers, a co-emulsifier, a short-chain alcohol ($C_1$-$C_5$), and a pH adjuster, for example an alkaline substance, such as sodium hydroxide.

The pH of the compositions according to the invention is generally comprised between 7 and 8.

In a further embodiment, the present invention provides the compositions as above described for use in therapy.

In a further embodiment, the present invention provides the compositions as above described for use in an anti-inflammatory, antirheumatic, antipyretic, and analgesic treatment.

In a further embodiment, the present invention provides the use of the compositions as above described in the preparation of a medicament for topical application to treat a pathological condition requiring an anti-inflammatory, antirheumatic, antipyretic, and analgesic treatment.

In a further embodiment, the present invention provides a method to treat a pathological condition requiring an anti-inflammatory, antirheumatic, antipyretic, and analgesic treatment, comprising administering a composition as above described to a patient in need thereof.

In these uses and methods, those diseases requiring topical applications of high and accurate doses of diclofenac are treated in a particularly advantageous way: such conditions take advantage from the more complete absorption, therefore with less dose dispersion and with a more intense and reproducible effect of the administered dose.

The invention further relates to a process for the preparation of a composition as above described, characterized in formulating diclofenac-epolamine at a concentration equal to or higher than 2% by weight, on the weight of the composition, in the presence of a suitable carrier for topical applications and possible co-formulation agents and excipients.

The invention is now described by the following non-limiting Examples.

EXPERIMENTAL

1. Preparation of the Compositions

Two hydrogel formulations for topical use have been prepared; the first with a 1.3% by weight concentration of diclofenac-epolamine (reference); the second, according to the present invention, with a 2.6% by weight concentration of diclofenac-epolamine. The compositions, keeping constant all the other ingredients, are shown in Table 1:

TABLE 1

|  | DHEP Gel 1.3% | DHEP Gel 2.6% |
|---|---|---|
| Active ingredient | % w/w | |
| DHEP | 1.3 | 2.6 |
| Excipients | % w/w | |
| Soybean lecithin (TOPCITHIN NGM) | 2.4 | 2.4 |
| Co-emulsifiers | 2.4 | 2.4 |
| Gelling agent | 1.5 | 1.5 |
| pH Adjuster | 2.53 | 2.53 |
| Preservative | 6 | 6 |
| Deionized water | 83.87 | 82.57 |

2. Percutaneous Absorption Test (IVPT Method)

The in vitro percutaneous absorption of diclofenac-epolamine from the compositions of Example 1 was quantitatively assessed, using dermatome human skin mounted in Franz™ vertical diffusion cells (static type). The assay was carried out in finished dose and occluded conditions, using each semisolid topical product (test and reference). This in vitro permeation assay was carried out on skin samples collected from 12 human donors. Each donor was treated in duplicate with 3 products (reference, test). Skin samples of 12 human female donors (aged from 27 to 59) of the same phenotype (Caucasian) were obtained by abdominoplasty. The collected samples were frozen immediately after collection and stored at −20 ° C. until the time of use in the in vitro assay. The skin samples were thawed and used after 1 hour at +4 ° C., and then were mounted in the diffusion cells without undergoing any other treatment following a randomization list. Prior to the application of the gel products, the integrity of the partial thickness skin samples was assessed by measuring the trans-epidermal water loss (TEWL). The measurement was directly performed on the cutaneous membrane considering for acceptance a value not exceeding 15 g/h m². Each skin sample was mounted in a horizontal position between the two cell parts generating two compartments, one on each side of the skin sample:

A donor compartment has a surface open to diffusion of 1.767 cm², carefully defined by size and shape, applied on the upper side of the skin.

A receptive compartment consisting of a compartment with a fixed volume of 7 ml with a sample gate for analysis and containing the receptive fluid, on which the skin sample was mounted. The two compartments are aligned and held in place by a horseshoe clamp.

The applied dose was of about 8.8 mg for each formulation directly studied on the cutaneous surface (1.767 cm²) according to a standard methodology.

The receptive room was immersed in a water bath (and kept at 32 ±1 ° C. The homogeneous distribution of the temperature of the receptive room was ensured by a magnetic stirrer (800 rpm, continuous stirring) with the cell unit mounted on a stirrer device. At each sampling time, 2.5 mL of liquid were sampled and substituted by an equivalent volume of fresh liquid.

Samples of the receptor phase were collected after 3, 6, 9, 12, 18, 24, 32, 40 and 48 hours.

At the end of this time frame, the amount of formulation remained on the skin surface was removed and the skin integrity (TEWL) was re-assessed to ensure that the membrane was not damaged.

The amounts of diclofenac in each liquid sample collected from the receptive room were quantified using high performance liquid chromatography (HPLC) validated with UV detection in order to determinate the relative Qn (Qn_Rel) expressed as %/cm² corresponding to the permeated total amount corrected by dosage.

The obtained results are shown in Table 2.

TABLE 2

| Donor For each donor the average of 2 samples is indicated | DHEP 2.6% max dose % in 48 h, normalized for dose | DHEP 1.3% max dose % in 48 h, normalized for dose | Difference between logarithms to the base e of the two % | EXP of the difference between logarithms to the base e of the two % |
|---|---|---|---|---|
| 1 | 35.84 | 29.21 | 0.20 | 1.23 |
| 2 | 70.31 | 61.10 | 0.14 | 1.15 |
| 3 | 55.36 | 45.01 | 0.21 | 1.23 |
| 4 | 81.84 | 68.46 | 0.18 | 1.20 |

TABLE 2-continued

| Donor For each donor the average of 2 samples is indicated | DHEP 2.6% max dose % in 48 h, normalized for dose | DHEP 1.3% max dose % in 48 h, normalized for dose | Difference between logarithms to the base e of the two % | EXP of the difference between logarithms to the base e of the two % |
|---|---|---|---|---|
| 5 | 23.49 | 25.00 | −0.06 | 0.94 |
| 6 | 33.89 | 32.01 | 0.06 | 1.06 |
| 7 | 48.31 | 42.98 | −0.02 | 0.98 |
| 8 | 23.61 | 19.51 | 0.19 | 1.21 |
| 9 | 51.76 | 59.15 | −0.13 | 0.88 |
| 10 | 18.94 | 15.46 | 0.20 | 1.23 |
| 11 | 34.91 | 34.58 | 0.01 | 1.01 |
| 12 | 55.60 | 42.79 | 0.26 | 1.30 |
| Arithmetic average (AA) | 44.49 | 40.13 | | 1.12 |
| Confidence interval at 90% on AA (CI 90%) | | | 1.045 | 1.19 |
| Geometric average (GA) | | | | 1.10 |
| Confidence interval at 90% on GA (CI 90%) | | | 1.01 | 1.19 |

It was observed than varying the concentration of diclofenac-epolamine in the gel from 1.3 to 2.6%, there is an average increase of the absorbed dose fraction, i.e. the percentage ratio between administered dose and absorbed dose, equal to about +11%. It is important to notice that the thus calculated percentage values are independent from the absolute amount of absorbed drug (whose value is necessarily higher in the case of the concentrated gel): this interference factor is eliminated in the calculation adopted, so that the comparative data of the two compositions are completely comparable; they show the higher ability of the gel according to the invention in obtaining a more complete absorption of the administered dose. For the purpose of comparability, all ingredients of the formulation, except diclofenac-epolamine, were kept constant; this led, in the gel according to the invention, to a reduction of the lecithin/diclofenac-epolamine ratio; i.e., with respect to the reference gel, the availability of lecithin to increase the solubility of diclofenac-epolamine decreased: despite this apparently unfavorable condition, the absorption amount registered from the gel according to the invention was higher than the one of the reference gel.

The invention claimed is:

1. A pharmaceutical composition for topical use comprising diclofenac in the form of salt with epolamine, diclofenac-epolamine, at a concentration of 2.6% by weight, based on the weight of the composition1, the composition comprising lecithin in a weight ratio ranging from 0.5:1 to 0.9:1 with respect to the diclofenac-epolamine salt.

2. The composition according to claim 1, in the form of hydrogel.

3. The composition according to claim 1, further comprising one or more emulsifiers.

4. A process for preparing the composition of claim 1, comprising formulating diclofenac-epolamine at a concentration of 2.6% by weight, based on the weight of the composition, in the presence of a suitable carrier for topical applications and possible co-formulation agents and excipients, wherein said carrier comprises lecithin, and the prepared composition comprises a lecithin weight ratio ranging from 0.5:1 to 0.9:1 with respect to the diclofenac-epolamine salt.

5. The process according to claim 4, wherein said carrier is a hydrogel.

6. A method of treating a pathological condition requiring an anti- inflammatory, antirheumatic, antipyretic, or analgesic treatment, comprising topically administering a composition of claim 1 to a patient in need thereof.

* * * * *